United States Patent [19]

Viout et al.

[11] 3,936,427

[45] Feb. 3, 1976

[54] MAGNESIUM SALT COPOLYMERS OF UNSATURATED DICARBOXYLIC ACID ANHYDRIDE AND UNSATURATED MONOMER HAVING A LIPOPHILE CHAIN

[75] Inventors: Andre Viout, Paris, France; David Esanu, deceased, late of Paris, France; Lydie Esther Samama, administratrix, Paris, France

[73] Assignee: Societe Anonyme dite: L'Oreal, Paris, France

[22] Filed: Mar. 25, 1974

[21] Appl. No.: 454,731

Related U.S. Application Data

[60] Division of Ser. No. 164,828, July 21, 1971, Pat. No. 3,860,700, which is a continuation-in-part of Ser. No. 136,238, April 21, 1971, abandoned, which is a continuation of Ser. No. 688,969, Dec. 8, 1967, abandoned.

[30] Foreign Application Priority Data

Dec. 8, 1966 Luxemburg............................ 52541

[52] U.S. Cl. ....................... 260/78.5 T; 260/78.5 R
[51] Int. Cl.$^2$ ......................................... C08F 222/02
[58] Field of Search... 260/78.5 R, 78.5 T, 29.6 WQ

[56] References Cited

UNITED STATES PATENTS

| | | | |
|---|---|---|---|
| 2,533,376 | 12/1950 | Jones.................................. | 260/78.4 |
| 2,542,542 | 2/1951 | Lippincott et al. ................... | 252/56 |
| 2,892,818 | 6/1959 | Lowe et al......................... | 260/78.5 |

*Primary Examiner*—John Kight, III
*Attorney, Agent, or Firm*—Cushman, Darby & Cushman

[57] ABSTRACT

Copolymers formed from an unsaturated dicarboxylic acid anhydride and an unsaturated monomer having a lipophile chain having a molecular weight of 4,000–100,000 are usefully employed to produce a water-in-oil emulsion which can be incorporated into cosmetic compositions.

3 Claims, No Drawings

MAGNESIUM SALT COPOLYMERS OF UNSATURATED DICARBOXYLIC ACID ANHYDRIDE AND UNSATURATED MONOMER HAVING A LIPOPHILE CHAIN

This is a division of application Ser. No. 164,828 filed July 21, 1971, now U.S. Pat. No. 3,860,700, which is a continuation-in-part of application Ser. No. 136,238, filed Apr. 21, 1971, now abandoned, which is a continuation of application Ser. No. 688,969, filed Dec. 8, 1967, now abandoned.

The present invention relates to copolymers made from an unsaturated dicarboxylic acid anhydride and an unsaturated monomer having a lipophile chain, the resulting copolymer having a molecular weight of about 4,000 to 100,000 and to the magnesium salt of said copolymers. The present invention is also related to water-in-oil emulsions made with said copolymers and the magnesium salt of said copolymers as well as to cosmetic compositions utilizing said water-in-oil emulsions.

In one embodiment of the present invention the copolymer has the formula

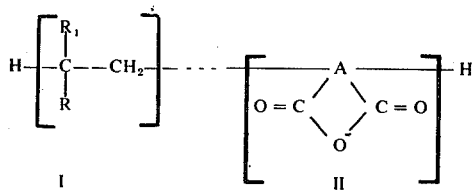

wherein:

A is selected from the group consisting of a. 

b. 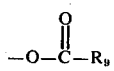   and c. 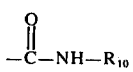

wherein
R$_2$ is selected from the group consisting of hydrogen and methyl, and
R is selected from the group consisting of
  d. alkyl having 8–18 carbon atoms,
  e.

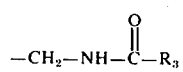

wherein R$_3$ is alkyl having 17 carbon atoms,
  f. —O—R$_4$ wherein R$_4$ is alkyl having 16 carbon atoms,
  g.

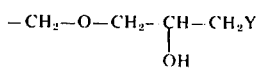

wherein Y is selected from the group consisting of

—O—C$_{12}$H$_{25}$, —S—C$_{12}$H$_{25}$ and —NH—C$_{18}$H$_{37}$ with the proviso that when R has the values of (d) to (g),
R$_1$ is hydrogen, and
h.

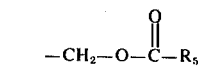

wherein R$_5$ is alkyl having 11–17 carbon atoms, with the proviso that when R has the value of (h), R$_1$ is selected from the group consisting of hydrogen and methyl, the molar ratio of monomeric units I:II is 1:1 and said copolymer has a molecular weight between 4,000–100,000.

In another embodiment of the present invention the copolymer has the formula

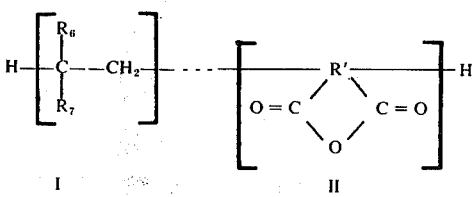

wherein
R′ represents

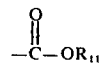

wherein R$_8$ is selected from the group consisting of hydrogen and methyl, and
R$_7$ is selected from the group consisting of
  a.

—O—C(=O)—R$_9$ wherein R$_9$ is alkyl having 18 carbon atoms
  b.

—C(=O)—NH—R$_{10}$ wherein R$_{10}$ is alkyl having 18 carbon atoms with the proviso that when R$_7$ has the values of (a)–(b),
R$_6$ represents hydrogen, and
  c.

—C(=O)—OR$_{11}$ wherein R$_{11}$ is alkyl having 12–18 carbon atoms, with the proviso that when R$_7$ has the value of (c), R$_6$ is selected from the group consisting of hydrogen and methyl, the molar ratio of monomeric units I : II ranges between 1–1.5 : 0.5–1 and said copolymer has a molecular weight ranging between 4,000–100,000.

Among the unsaturated dicarboxylic acid anhydrides usefully employed in the present invention to prepare said copolymers are maleic anhydride, itaconic anhydride, citraconic anhydride, acrylic anhydride, methacrylic anhydride and acrylic/methacrylic anhydride having the formula:

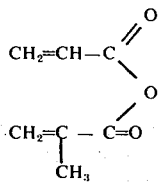

Among the unsaturated monomers having a lipophile chain which are usefully employed together with the unsaturated dicarboxylic acid anhydride to produce the copolymers of this invention are α-olefins having from 10–20 carbon atoms; acrylic esters and methacrylic esters having 15–22 carbon atoms; vinyl esters, allyl esters and methallyl esters having 12–20 carbon atoms; acrylamides and methacrylamides which are N-sunstituted by alkyl having 18 carbon atoms; N-allyl and N-methallyl alkylamides wherein the alkyl moiety has 17 carbon atoms; alkyl-vinyl ethers wherein the alkyl moiety has 16 carbon atoms; and the products obtained by condensing alcohols such as 1-dodecanol, amines such as stearyl amine and alkyl mercaptans wherein the alkyl moiety has 12 carbon atoms on allylglycidyl ether.

Representative unsaturated monomers having a lipophilic chain include 1-octadecene, 1-hexadecene, 1-eicosene, dodecyl methacrylate, allyl stearate, N-stearylacrylamide, N-allyl stearamide, 1-allyloxy-3-dodecylthio-2-propanol, 1-allyloxy 3-dodecyloxy 2-propanol, 1-allyloxy 3-stearylamino 2-propanol, cetyl vinyl ether, vinyl stearate, 1-decene, and methallyl laurate.

It will be appreciated by those skilled in the art that the unsaturated monomer having a lipophile chain can be generally categorized into two groups, one group being those monomers which are capable of homopolymerization, in which event the molar ratio of said homopolymerizable unsaturated monomer to unsaturated dicarboxylic acid anhydride can vary widely, for instance between 1–1.5 : 0.5–1. The other group includes those monomers which are not capable of homopolymerisation, in which event the molar ratios of said nonhomopolymerizable unsaturated monomer to unsaturated dicarboxylic acid anhydride is 1 : 1.

In accordance with the present invention, the polymerization reaction can be carried out in an anhydrous solvent such as benzene, toluene, dichloroethane, methylchloroform, methyl ethyl ketone, and methylisobutyl ketone. Other known methods of polymerization can also be used. The concentration of monomers with respect to the solvent is preferably from 25% to 50% by weight.

The polymerization rate is increased by using a catalyst, such as benzoyl peroxide, lauroyl peroxide, or azo-bis-isobutyronitrile, which can be added to the reaction mixture at the rate of about 1 to 6% and preferably between 2 and 4% of the weight of the mnomers. After polymerization, the resulting copolymer is isolated either by evaporating the solvent, or by precipitation in an appropriate solvent, and then dried. Illustrative appropriate solvents are low molecular weight alcohols comprising 1 to 6 carbon atoms such as propyl alcohol but isopropanol is generally prefered.

Also in accordance with the invention the magnesium salt of the copolymer defined above can be prepared by double decomposition, for example, by first preparing the dialkaline salt of the copolymers, which is then reacted with a solution of magnesium chloride.

The magnesium salt can also be prepared by reacting magnesium acetate with the copolymer as defined above.

The present invention also provides an emulsion of the "water-in-oil" type, which is obtained by dissolving a copolymer as defined above which can be in the form of the corresponding magnesium salt, in an oil to be emulsified and then adding a suitable amount of water.

Emulsions according to the invention can be prepared by adding the emulsifier to oil which has first been heated to 90°C, and then stirring vigorously while adding the desired quantity of water, also heated to 90°C, after which it is cooled, while still stirring.

The water-in-oil type emulsion made in accordance with the invention can contain from 30 to 60% water by weight, with the emulsifier constituting from 6.5 to 14% by weight and with the oil phase constituting between 18–60% by weight, all percentages being based on the total weight of the emulsion.

The oil phase of the emulsion can consist, for example, of a hydrocarbon oil, such as paraffin oil, petrolatum, and perhydrosqualene; solutions of microcrystalline wax in paraffin oil; and animal or vegetable oils such as horse oil, lard, sweet almond oil, and calophyllum oil. These oils are readily absorbed by the skin. Saturated esters which are incapable of becoming rancid and are good penetrants, such as isopropyl palmitate isopropyl myristate, ethyl palmitate and the like as well as silicone oils which are soluble in other oils are also usefully employed.

In accordance with the invention, these emulsions can also contain suitable additives.

The cosmetic compositions of the present invention contain at least one copolymer as defined above including the corresponding magnesium salt thereof.

These cosmetic compositions are preferably emulsions of the water-in-oil type and are particularly interesting because they prevent dessication.

In order that the invention may be better understood, several examples will now be described, purely by way of illustration, without suggesting that the scope of the invention is limited to the details thereof. Unless otherwise specified, all parts and percentages are by weight.

EXAMPLE 1

Preparation of a 50% maleic anhydride/50% 1-octadecene copolymer (molar ratio):

1700 G of 1-octadecene, 300 g of maleic anhydride and 80 g of benzoyl peroxide in solution in 2000 g of anhydrous benzene are introduced into a flask equipped with an agitator, a thermometer, a condenser, and a tube for introducing nitrogen.

This is heated slowly to its boiling point and kept at reflux for 8 hours.

After cooling, isopropanol is used to precipitate the copolymer. After drying, the yield is 91% of the desired copolymer in the form of a waxy colorless mass which is soluble in the oils, and particularly in paraffin oil, isopropyl myristate, ethyl palmitate, etc.

By measuring the anhydride function, it is found that the copolymer contains anhydride in an amount of 28% by weight. The molecular weight of the copolymer is $\overline{M}_w = 18,000$.

EXAMPLE 2

Preparation of the magnesium salt of the copolymer prepared in Example 1

35 G of the copolymer produced in Example 1 and 65 g of paraffin oil were introduced into a vessel thermostatically maintained at about 100°C. This was stirred for 24 hours until the copolymer was completely dissolved in the oil. About 200 g of boiling water were then added.

While stirring vigorously and keeping the mixture boiling, 109 g of a 10.3% solution of caustic potash were poured into the mixture.

A concentrated solution containing 20.2 g of $Cl_2Mg$, $6H_2O$ was then added drop by drop.

At the end of this addition the water settled at the bottom of the vessel.

The magnesium salt of the copolymer has formed, in the presence of oil and water, a water-in-oil emulsion, which separates out at the top of the water.

This was then washed several times with 200 ml of boiling water each time and dried on calcium chloride or under vacuum in a water-bath.

The resulting product when cold is a thick paste.

EXAMPLE 3

Preparation of a 50% maleic anhydride/50% 1-hexadecene copolymer (molar ratio)

68.5 G of 1-hexadecene, 15 g of maleic anhydride, and 6 g of benzoyl peroxide in solution in 150 g of anhydrous benzene, were introduced into a flask provided with an agitator, a thermometer, a condense, and a tube for introducing nitrogen.

The mixture was brought to its boiling point and kept at reflux for 24 hours.

After cooling, the copolymer was precipitated, using isopropanol.

The yield was 85% of the copolymer sought, and took the form of a waxy mass soluble in oil and particularly in paraffin oil, isopropyl myristate and ethyl palmitate.

By measurement of the anhydride function, it was found that the copolymer had a 30% anhydride content by weight. The molecular weight is $\overline{M}_w = 10,000$.

EXAMPLE 4

Preparation of the magnesium salt of the copolymer of Example 3

By using the same process as that described in Example 2, the magnesium salt of the copolymer was obtained. This copolymer, when cold, is a thick paste.

EXAMPLE 5

Preparation of a 50% maleic anhydride/50% 1-eicosene copolymer (molar ratio)

The procedure followed was the same as that described in Example 1 except that 1-eicosene was employed rather than 1-octadecene.

The result was an 89% yield of the desired copolymer, which was soluble in oil and particularly in paraffin oil, isopropyl myristate and ethyl palmitate.

By measurement of the anhydride function it is found that the copolymer contains 26% anhydride by weight. The molecular weight is $\overline{M}_w = 20,000$.

EXAMPLE 6

Preparation of the magnesium salt of the copolymer of Example 5

By using the same process as that described in Example 2, the magnesium salt of the copolymer of Example 5 was produced in the form of a thick paste.

EXAMPLE 7

Preparation of the magnesium salt of a copolymer by the magnesium acetate method 28 Parts of maleic anhydride and 72 parts of 1-octadecene were copolymerized using essentially the same procedures outlined in Example 1. The resulting copolymer was then precipitated employing isopropanol and the resulting maleic anhydride/1-octadecene copolymer exhibited an anhydride index of 295.

43.4 G of this polymer were dissolved in a boiling water-bath in 80.6 g of vaseline oil. The mixture was placed in a flask, agitated, and heated in a bath of calcium chloride. When the temperature reached 100°C, a solution of 31.5 g of $Mg(C_2H_3O_2)_2.4H_2O$ in 186 g of water is added, drop by drop, over a period of 20 minutes. The reacting acetic acid was then steam distilled over a period of 6 hours, while keeping the temperature of the mixture at about 120°–130°C.

Analysis of the water of distillation indicated that it contained 228 mmols of acetic acid, which indicates that 77.5% of the magnesium acetate had reacted.

The resulting product was then washed seven times in boiling water, using 500 ml of water each time, and the magnesium content of the wash water was measured. 31.6 mmols of magnesium, indicative of 21.5% of the magnesium introduced, was found.

The resulting product was dehydrated in a boiling water-bath under the vacuum created by a water-jet pump.

EXAMPLE 8

Preparation of the magnesium salt of a maleic anhydride/1-octadecene copolymer by double decomposition:

The starting polymer was produced by copolymerizing 28 parts of maleic anhydride and 72 parts of 1-octadecene, and precipitated in a suitable solvent. Its anhydride index was 297.

350 G of this copolymer was dissolved in 1,400 g of vaseline oil in a boiling water-bath, and 1,500 g of deionized water was then added.

While stirring vigorously, and boiling, 1,316 g of 9.2% of caustic potash were added, followed by 219.3 g of $Cl_2Mg.6H_2O$ in 470 g of water.

The mixture was then washed 3 times with five liters of pure water, the percentage of each of the following in the decanted waters was determined:
 the chloride, by the Charpentier-Volhard method,
 the magnesium with anaklepton (disodic salt of ethylene diamine teracetic acid).

2.180 Mols of chloride, that is 101% of the starting quantity, and 0.196 mols of magnesium, that is, 18% of the starting quantity were found.

The basicity of the potassium salt was measured with hydrochloric acid in the presence of phenolphtalein in a miscible solvent, and showed that 95% of the starting potash had reacted with the copolymer.

The distribution of the reactive groups of the polymer obtained at the end of the reaction was as follows:
  82% in the form of the magnesium salt,
  13% in the form of the potassium salt,
  5% in the form of anhydride.

The fact that the pH value of the decanted water containing the magnesium salt prepared by double decomposition may be alkaline as a consequence of the diffusion of the potassium ions may be disadvantageous when these products are used as emulsifiers.

It has been found that by incorporating a certain quantity of the copolymer in the form of an anhydride in the magnesium salt, the pH of the wash waters can be brought to a nearly neutral value.

The procedure is as follows:

500 Parts of deionized water are added to 100 parts of the magnesium salt obtained by double decomposition, and this is boiled for 10 minutes. The pH value of the decanted water is then measured. The same operation is repeated while incorporating increasing quantities of the copolymer in the form of the anhydride and the pH value of the water is compared with the quantity of the anhydride added.

The following table shows the pH value of the wash water of the magnesium salt as a function of the quantity of copolymer in its anhydride form which is added to the magnesium salt of the polymer.

| Quantity of magnesium salt of the polymer | Quantity of copolymer added in the anhydride form | pH of the wash-waters |
|---|---|---|
| 100 | 0 | 8.3 |
| 100 | 10 | 8.2 |
| 100 | 20 | 8 |
| 100 | 30 | 7.9 |
| 100 | 40 | 7.5 |
| 100 | 50 | 7.1 |

EXAMPLE 9

Preparation of a 31% maleic anhydride/69% dodecyl methacrylate copolymer: (Molar ratio)

100 G of dodecyl methacrylate, 17.6 g of maleic anhydride, and 4.68 g of benzoyl peroxide in solution in 118 g of anhydrous benzene, are introduced into a flask provided with an agitator, a thermometer, a condenser, and a tube for introducing nitrogen. This was heated until it boiled and was kept at reflux for 22 hours.

After cooling, the copolymer was precipitated with isopropanol. After drying, 85% of the yield consisted of the desired copolymer in the form of a waxy mass which was soluble in paraffin oil.

By measuring the anhydride function it was found that the copolymer contained 14.8% anhydride by weight. The molecular weight is $\overline{M}_w = 40,000$.

EXAMPLE 10

Preparation of the magnesium salt of the copolymer prepared according to Example 9

The magnesium salt of the copolymer of Example 9 was obtained in the form of a viscous paste by using the same procedure as that described in Example 2.

EXAMPLE 11

Preparation of a 50% itaconic anhydride/50% allyl stearate copolymer (molar ratio)

104 G of allyl stearate, 18 g of itaconic anhydride and 7.05 g of benzoyl peroxide in solution in 150 g of methyl chloroform were introduced into a flask provided with an agitator, a thermometer, a condenser and a tube for introducing nitrogen and the resulting mixture was heated to reflux for 16 hours.

After cooling, the copolymer was precipitated with ispropanol.

After drying, the yield was 94% of the desired copolymer in the form of a waxy mass, soluble in paraffin oil.

By measurement of the anhydride function it was determined that the copolymer contained 25.7% anhydride by weight. The molecular weight is $\overline{M}_w = 30,000$

EXAMPLE 12

Preparation of a 50% citraconic anhydride/50% N-stearylacrylamide copolymer (molar ratio)

The procedure is the same as in Example 1. The result is a 75% yield of the desired copolymer, in the form of a powder which is soluble in paraffin oil.

By measurement of the anhydride function it was found that the copolymer contained 25.9% anhydride by weight. The molecular weight is $\overline{M}_w = 48,000$.

EXAMPLE 13

Preparation of the magnesium salt of the copolymer according to Example 12

By using essentially the same process as in Example 2, the magnesium salt of the copolymer of Example 12 was produced in the form, when cold, of a viscous paste.

EXAMPLE 14

Preparation of a 50% acrylic anhydride/50% N-allylstearamide copolymer (molar ratio)

The procedure was the same as in Example 11.

The result was a 96% yield of the desired copolymer, which is soluble in paraffin oil.

By measurement of the anhydride function it was found that the copolymer contained 23% anhydride by weight. The molecular weight is $\overline{M}_w = 62,000$.

EXAMPLE 15

Preparation of a 50% methacrylic anhydride/50% 1-allyloxy-3-dodecylthio-2-propanol copolymer (molar ratio)

The process is essentially the same as described in Example 11. The result is a 92% yield of the desired copolymer. By measurement of the anhydride function it is found that the copolymer contains 30% anhydride by weight. The molecular weight is $\overline{M}_w = 32,000$.

EXAMPLE 16

Preparation of a 50% mixed acrylic-methacrylic anhydride/50% 1-allyloxy-3 dodecyloxy-2 propanol copolymer (molar ratio)

The method is essentially the same as that described in Example 11. The result is a 98% yield of the desired copolymer, which is soluble in paraffin oil. The molecular weight is $\overline{M}_w = 54,000$.

By measurement of the anhydride function it is found that the copolymer contains 30% anhydride by weight.

EXAMPLE 17

Preparation of a 50% citraconic anhydride/50% 1-allyloxy 3-stearylamino-2-propanol copolymer (molar ratio)

The procedure is essentially the same as in Example 11.

The result is 95% yield of the desired copolymer, which is soluble in paraffin oil.

By measurement of the anhydride function it is found that the copolymer contains 29.5% anhydride by weight. The molecular weight is $\overline{M}_w = 18,000$.

EXAMPLE 18

Preparation of a 50% citraconic anhydride/50% allyl stearate copolymer (molar ratio)

This process is essentially the same as that described in Example 11. The result is a 95% yield of the desired copolymer, which is soluble in paraffin oil.

By measurement of the anhydride function it is determined that the copolymer contains 25% anhydride. The molecular weight is $\overline{M}_w = 17,000$.

EXAMPLE 19

Preparation of the magnesium salt of the copolymer according to Example 18

The magnesium salt of the copolymer of Example 18 is obtained in the same way as in Example 2. When cold, it is in the form of a thick paste.

EXAMPLE 20

Preparation of a 50% maleic anhydride/50% cetylvinylether copolymer (molar ratio)

The process is essentially the same as that described in Example 1.

The result is a 92% yield of the desired copolymer, which is soluble in paraffin oil.

By measurement of the anhydride function, it is found that the copolymer contains 28% anhydride by weight. The molecular weight is $\overline{M}_w = 25,000$.

EXAMPLE 21

Preparation of the magnesium salt of the copolymer according to Example 20

The magnesium salt of the copolymer of Example 20 is obtained in the same way as in Example 2 and, when cold, takes the form of a rather stiff paste.

EXAMPLE 22

Preparation of a 28% maleic anhydride/72% vinyl stearate copolymer (molar ratio)

The process is essentially the same as that described in Example 1. The result is an 88% yield of the desired copolymer which is soluble in paraffin oil.

By measurement of the anhydride function, it is found that the copolymer contains 11% anhydride by weight. The molecular weight is $\overline{M}_w = 45,000$.

EXAMPLE 23

Preparation of the magnesium salt of the copolymer according to Example 22

The magnesium salt of the copolymer of Example 22 is obtained in essentially the same way as in Example 2 and, when cold, takes the form of a viscous paste.

EXAMPLE 24

Preparation of a 50% maleic anhydride/50% 1-decene (molar ratio)

37 G of 1-decene at 94.6%, 12.25 g of maleic anhydride and 52 g of anhydrous toluene are introduced into a flask equipped with an agitator, a thermometer, a condenser and a tube for introducing nitrogen. To this mixture 2.84 g of benzoyl peroxide in solution in 19 g of toluene are introduced.

This solution is heated at 100°C for 30 hours.

After cooling, the solution is poured in 1.2 kg of petroleum ether. The precipitated powdered polymer is then dissolved in toluene and reprecipitated by petroleum ether. After filtration and drying, the yield was 45%. The molecular weight is $\overline{M}_w = 18,000$.

EXAMPLE 25

Preparation of a 50% maleic anhydride/50% methallyl laurate (molar ratio)

The procedure is the same as that described in Example 24.

The starting materials are:
63.6 g methally laurate
12.25 g maleic anhydride
2.53 g of benzoyl peroxide, and
105 g of toluene.

After cooling, the mixture is poured into 1.2 kg of isopropanol.

The yield was 40% and the molecular weight of the copolymer is $\overline{M}_w = 24,000$.

By measuring the anhydride function, it is found that the copolymer contains 26.7% anhydride by weight.

EXAMPLE 26

Preparation of a 50% maleic anhydride/50% 1-octadecene (molar ratio)

1,500 G of 1-octadecene, 300 g of maleic anhydride and 20 g of benzoyl peroxide in solution in 2,000 g of anhydrous methylchloroform are introduced into a flask equipped with an agitator, a thermometer, a condenser and a tube for introducing nitrogen.

This mixture is heated to its boiling point and kept at reflux for 12 hours.

After cooling, isopropanol is used to precipitate the copolymer. After drying the yield is 95%.

By measuring the anhydride function, it is found that the copolymer contains 28% anhydride by weight. The molecular weight is $\overline{M}_w = 53,000$.

EXAMPLE 27

Preparation of a 50% maleic anhydride/50% 1-hexadecene (molar ratio)

The procedure is the same as that described in Example 26.

The starting materials are:
57 g 1-hexadecene
15 g maleic anhydride
0.43 g benzoyl peroxide 23 g anhydrous methylchloroform.
The yield is 97%.

By measuring the anhydride function it is found that the copolymer contains 30% anhydride by weight. The molecular weight is $\overline{M}_w = 97,000$.

EXAMPLE 28

Preparation of a 50% maleic anhydride/50% 1-octadecene (molar ratio)

The procedure is the same as that described in Example 26 but the reflux time is 14 hours.
The starting materials are:
500 g 1-octadecene
100 g maleic anhydride
10 g benzoyl peroxide and
3500 g anhydrous toluene.
The yield is 95%.

By measuring the anhydride function it is found that the copolymer contains 28.2% anhydride by weight. The molecular weight is $\overline{M}_w = 4,000$.

The following examples illustrate water-in-oil emulsions and their preparation as well as cosmetic compositions embodying the same, all in accordance with the present invention.

EXAMPLE A

A fluid cream, in accordance with the present invention, was prepared by adding 40 g of water, which had first been heated to 90°C, to the following mixture:

| | |
|---|---|
| Copolymer produced in accordance with Example 2 | 8.4 g |
| Paraffin oil | 51.6 g |

This mixture was vigorously agitated, and then cooled while it was still being agitated.

EXAMPLE B

A make-up base according to the invention was prepared by adding 34 g of water, which had first been heated to 90°C, to the following mixture:

| | |
|---|---|
| Copolymer produced in accordance with Example 4 | 8.3 g |
| Vaseline | 25.5 g |
| Paraffin oil | 20.3 g |
| Perhydrosqualene | 8.2 g |
| Titanium oxide | 2 g |
| Ocher | 1.5 g |
| Perfume | 0.2 g |

This mixture was vigorously agitated and cooled while still being agitated.

EXAMPLE C

A cheek rouge, in accordance with the present invention was prepared by adding 40 g of water, which had first been heated to 90°C, to the following mixture:

| | |
|---|---|
| Copolymer produced in accordance with Example 1 | 10 g |
| Isopropyl palmitate-stearate | 10 g |
| Vaseline | 18 g |
| Paraffin oil | 16.25 g |
| Microcrystalline wax | 2 g |
| Pigments | 2 g |
| Perfume | 0.25 g |
| Silicone oil, sold under the designation "SI 555" by Societe Industrielle des Silicones (methyl phenyl polysiloxane) | 1.5 g |

This mixture was vigorously agitated and cooled while still agitating.

EXAMPLE D

A fluid cream for use on the finger-nails in accordance with the present invention was prepared by adding 30 g of water which had first been heated to 90°C to the following mixture:

| | |
|---|---|
| Copolymer produced in accordance with Example 2 | 8.75 g |
| Copolymer produced in accordance with Example 1 | 3.30 g |
| Paraffin oil | 22.75 g |
| Isopropyl myristate | 29 g |
| Liquid lanolin | 4 g |
| Microcrystalline wax | 2 g |
| Perfume | 0.2 g |

This mixture was vigorously agitated and cooled while agitation was continued.

EXAMPLE E

A night cream in accordance with the present invention was prepared by adding 35 g of water, which had first been heated to 90°C, to the following mixture:

| | |
|---|---|
| Copolymer produced in accordance with Example 5 | 14 g |
| Purcellin oil | 2 g |
| Perhydrosqualene | 18 g |
| Bleached ozokerite | 4 g |
| Paraffin oil | 27 g |

This mixture was vigorously agitated and then cooled while agitation was continued.

EXAMPLE F

A fluid cream in accordance with the present invention was prepared by adding 59.7 g of water, which had first been heated to 90°C, to the following mixture:

| | |
|---|---|
| Copolymer produced in accordance with Example 8 | 8 g |
| Paraffin oil | 30 g |
| Microcrystalline wax | 2 g |
| Perfume | 0.3 g |

This mixture was vigorously agitated and then cooled while agitation was continued.

EXAMPLE G

A cream in accordance with the present invention and having the following composition is prepared:

| | |
|---|---|
| Copolymer according to Example 19 | 7.7 g |
| Paraffin oil | 46 g |
| Water (initially heated to 90°C) | 46.3 g |

This mixture was vigorously agitated and then cooled while agitation continued.

EXAMPLE H

A liquid cream of the present invention is prepared by adding 54 g of water, which has been heated to 90°C, to the following mixture:

| Copolymer produced in accordance with Example 19 | 10 | g |
| Copolymer produced in accordance with Example 18 | 4 | g |
| Paraffin oil | 29 | g |
| Microcrystalline wax | 3 | g |

This mixture is vigorously agitated and cooled while agitation is continued.

EXAMPLE I

A hand cream of the present invention is prepared by adding 48 g of water, which has been heated to 90°C, to the following mixture:

| Copolymer according to Example 13 | 6.7 | g |
| Paraffin oil | 42.1 | g |
| Titanium oxide | 3 | g |
| Perfume | 0.2 | g |

This mixture is vigorously agitated, and cooled while agitation is continued.

EXAMPLE J

A mixture base of the present invention is prepared by adding 35 g of water which has first been heated to 90°C to the following mixture:

| Copolymer prepared in accordance with Example 23 | 8.5 | g |
| Paraffin oil | 44.5 | g |
| Perhydrosqualene | 8.3 | g |
| Titanium oxide | 2 | g |
| Ocher | 1.5 | g |
| Perfume | 0.2 | g |

This mixture is vigorously agitated and cooled while agitation is continued.

EXAMPLE K

A fluid cream is prepared by pouring 40 g of water, which had first been heated to 90°C, to the following mixture:

| Copolymer produced in accordance with Example 2 | 8.4 | g |
| Paraffin oil | 50 | g |
| Silicon oil sold under the designation of "S I 555" by Societe Industrielle des Silicones (methyl phenyl polysiloxane) | 1.6 | g |

This mixture was vigorously agitated and cooled while still being agitated.

EXAMPLE L

A fluid cream is prepared by pouring 60 g of water, which had first been heated to 90°C, to the following mixture:

| Copolymer produced in accordance with Example 8 | 8 | g |
| Paraffin oil | 28 | g |
| Microcrystalline wax | 2.5 | g |
| Silicon oil sold under the tradename "SI 200", by Societe Industrielle des Silicones (dimethylpolysiloxane) | 1.5 | g |

This was vigorously agitated and cooled while still being agitated.

EXAMPLE M

A fluid cream embodying the invention is prepared by adding 30 g of water which had first been heated to 90°C to the following mixture:

| Copolymer produced in accordance with Example 24 | 12 | g |
| Triglyceride capro-caprylate | 54 | g |
| Microcrystalline wax | 4 | g |

This mixture was vigorously agitated, and then cooled while it was still being agitated.

EXAMPLE N

A fluid cream of the present invention is prepared by adding 33 g of water which had first been heated to 90°C to the following mixture:

| Copolymer produced in accordance with Example 25 | 11 | g |
| Microcrystalline wax | 2 | g |
| Triglyceride capro-caprylate | 50 | g |
| Isopropyl myristate | 4 | g |

This mixture was vigorously agitated and then cooled while it was still being agitated.

What is claimed is:

1. The magnesium salt of a copolymer having the formula

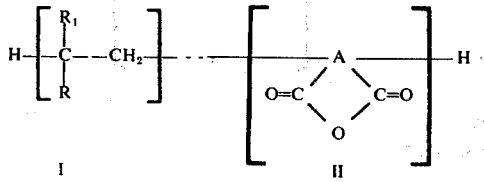

wherein

A is selected from the group consisting of a. 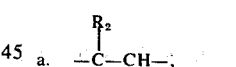

b. 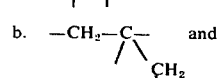 and c. 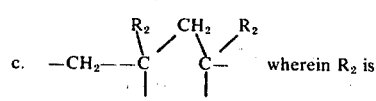 wherein $R_2$ is wherein $R_2$ is selected from the group consisting of hydrogen and methyl, and R is selected from the group consisting of (d) alkyl having 8–18 carbon atoms, e.

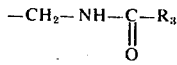

wherein $R_3$ is alkyl having 17 carbon atoms, f. $-O-R_4$ wherein $R_4$ is alkyl having 16 carbon atoms, g.

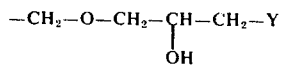

wherein Y is selected from the group consisting of —O—$C_{12}H_{25}$, —S—$C_{12}H_{25}$ and —NH—$C_{18}H_{37}$ with the proviso that when R has the values of (d) to (g), $R_1$ is hydrogen, and h.

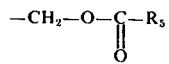

wherein $R_5$ is alkyl having 11–17 carbon atoms, with the proviso that when R has the value of (h), $R_1$ is selected from the group consisting of hydrogen and methyl, the molar ratio of monomeric units I:II is 1:1 and said copolymer has a weight average molecular weight ranging between 4,000–100,000.

2. The magnesium salt of a copolymer having the formula

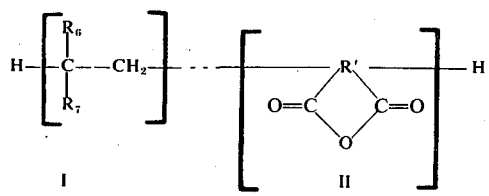

wherein
R′ represents

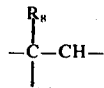

wherein $R_8$ is selected from the group consisting of hydrogen and methyl, and $R_7$ is selected from the group consisting of a.

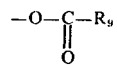

wherein $R_9$ is alkyl having 18 carbon atoms, b.

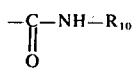

wherein $R_{10}$ is alkyl having 18 carbon atoms, with the proviso that when $R_7$ has the values of (a)–(b), $R_6$ represents hydrogen, and c.

wherein $R_{11}$ is alkyl having 12–18 carbon atoms, with the proviso that when $R_7$ has the value of c., $R_6$ is selected from the group consisting of hydrogen and methyl,
the molar ratio of monomeric units I:II ranges between 1–1.5: 0.5–1 and said copolymer has a weight average molecular weight ranging between 4,000–100,000.

3. The magnesium salt of a copolymer of (1) an unsaturated dicarboxylic acid anhydride selected from the group consisting of maleic anhydride, itaconic anhydride, citraconic anhydride, acrylic anhydride, methacrylic anhydride and acrylic-methacrylic anhydride and (2) a copolymerizable unsaturated monomer having a lipophile chain and being selected from the group consisting of 1-octadecene, 1-hexadecene, 1-eicosene, dodecyl methacrylate, allyl stearate, N-stearyl acrylamide, N-allyl stearamide, 1-allyl-oxy-3-dodecylthio-2-propanol, 1-allyloxy-3-dodecyloxy-2-propanol, 1-allyloxy-3-stearylamino-2-propanol, cetyl vinyl ether, vinyl stearate, 1-decene and methallyl laurate, said copolymer having a weight average molecular weight ranging from 4,000–100,000.

* * * * *